United States Patent [19]

Dawson et al.

[11] Patent Number: 5,018,223

[45] Date of Patent: May 28, 1991

[54] NON-FOGGING GOGGLES

[75] Inventors: Chris R. Dawson; Gerald R. Parks; John Dondero, all of Chula Vista, Calif.

[73] Assignee: John R. Gregory, Chula Vista, Calif.

[21] Appl. No.: 519,911

[22] Filed: May 7, 1990

Related U.S. Application Data

[63] Continuation-in-part of Ser. No. 410,041, Sep. 20, 1989, abandoned.

[51] Int. Cl.$^5$ ............................................. A61F 9/02
[52] U.S. Cl. ............................................ 2/436; 2/441; 351/62
[58] Field of Search .................. 2/435, 436, 437, 439, 2/441, 443, 440, 8, 9, 426; 351/62

[56] References Cited

U.S. PATENT DOCUMENTS

| | | | |
|---|---|---|---|
| 1,562,350 | 11/1925 | Luckey | 2/435 X |
| 2,665,685 | 1/1954 | Wood et al. | 128/75 |
| 3,012,248 | 12/1961 | Kleinman | 2/436 |
| 3,488,215 | 1/1970 | Shepherd et al. | 2/435 X |
| 3,505,680 | 4/1970 | Ring | 2/14 |
| 3,591,864 | 4/1971 | Allsop | 2/14 K |
| 3,945,044 | 3/1976 | McGee et al. | 2/436 |
| 4,414,693 | 11/1983 | Brody | 2/435 |
| 4,455,689 | 6/1984 | Boyer | 2/434 |
| 4,942,629 | 7/1990 | Stadlmann | 2/435 |

FOREIGN PATENT DOCUMENTS

| | | | |
|---|---|---|---|
| 2408982 | 9/1975 | Fed. Rep. of Germany | 2/436 |
| 0207060 | 8/1989 | Japan | 2/439 |

OTHER PUBLICATIONS

"Non-Misting Safety Goggle" Manufacturing Optician, vol. 15, No. 6, p. 275, Mar. 1962.

Primary Examiner—Peter Nerbun
Attorney, Agent, or Firm—Henri J. A. Charmasson

[57] ABSTRACT

A non-fogging goggles includes a double lens that consists of a pair of two spaced-apart lenses that have an air interstice therebetween and in which the inner surface of the outer lens is coated with a metal film. The metal coating is preferably made of gold and is vacuum-deposited on the outer lens. The body heat radiated by the user is reflected on the metal film and reduces the temperature differential between the inner lens and the area enclosed by the goggles, thereby preventing fogging of the inner lens. The radiated heat will also contribute in maintaining the temperature of the lens of any corrective eyeglasses worn under the goggles.

3 Claims, 1 Drawing Sheet

NON-FOGGING GOGGLES

PRIOR APPLICATION

This is a continuation-in-part application of copending application serial number 07/410,041 filed Sept. 20, 1989, now abandoned.

FIELD OF THE INVENTION

The present invention relates to protective eye-wear and more particularly to goggles for use in moisture-laden environments.

BACKGROUND OF THE INVENTION

Fogging by the condensation of water vapor on goggles has resulted in serious accidents and more generally has been an inconvenience to skiers, motorcyclists and other users.

One solution to this problem has been provided by goggles as disclosed in U.S. Pat. Nos. 4,414,693; 3,591,864; 3,505,680; 3,488,215; 2,665,686 and 1,562,350.

Attempts at fogging prevention have included chemical treatment, double lenses, forced air and electrically heated lenses.

In U.S. Pat. No. 4,414,693, there is disclosed an optical device wherein fogging is prevented by means of transparent hydrophylic polymer integrated with the transmissive surface thereof.

The safety goggle claimed in U.S. Pat. No. 3,505,680 comprises a pair of spaced lenses with an insulating air space therebetween.

The non-fogging goggles described in U.S. Pat. No. 3,591,864 also includes a pair of spaced apart lenses having a dead air space therebetween and a dehumidifier in the form of a tightly woven wire mesh portion made of a flexible metal of higher thermoconductivity.

A double-lens goggle is further recited in U.S. Pat. No. 1,562,350, wherein the inner sides of the interstice between the two lenses are covered with gelatin.

In *Manufacturing Optician*, Vol. 15, No. 6, March, 1962, p.275, a double-lens goggle is described, which also includes a small metal disc inserted into each side of the goggle frame. The metal disc acts as a condenser and draws the internally created moisture.

While the arrangements utilized in the aforementioned patents have a number of advantages, they have been found to be defective in the long run. Chemical treatment, such as lens coating, has turned out not to be permanent. Long-term exposure to moisture or large differences of temperature between the external atmosphere and the interstice of a double-lens goggle results in fogging. Forced air devices and electrically heated lenses are not practical for skier goggles and are also expensive.

SUMMARY OF THE INVENTION

It is therefore the primary object of the present invention to provide goggles with an improved system to prevent fogging.

Another object of the present invention is to provide improved double-lens goggles in which fogging of the viewing are is prevented by a metal film deposited against the inner face of the reflective outer lens.

It is still a further object of the invention to provide improved goggles in which fogging of the lens is prevented by means of the body heat radiated by the user and reflected upon the metal film, thereby maintaining the same temperature on the inner lens or the lenses of eyeglasses worn under the goggles as in the interstice defined by the two lenses of the double lens.

Accordingly, non-fogging goggles, in accordance with the present invention, include a lens of which the inner surface is coated with a metal film. The metal coating is preferably made of gold and is vacuum-deposited on the outer lens. The body heat radiated by the user is reflected on the metal film and reduces the differential between the ambient temperature and the area enclosed by the goggles, thereby preventing fogging of the inner surface of the lens.

BRIEF DESCRIPTION OF THE DRAWING

These and other objects of the present invention will become more apparent from a reading of the following specification and claims in connection with the accompanying drawing in which:

DESCRIPTION OF THE PREFERRED EMBODIMENT OF THE INVENTION

Figures 1, 2, 3, 4:
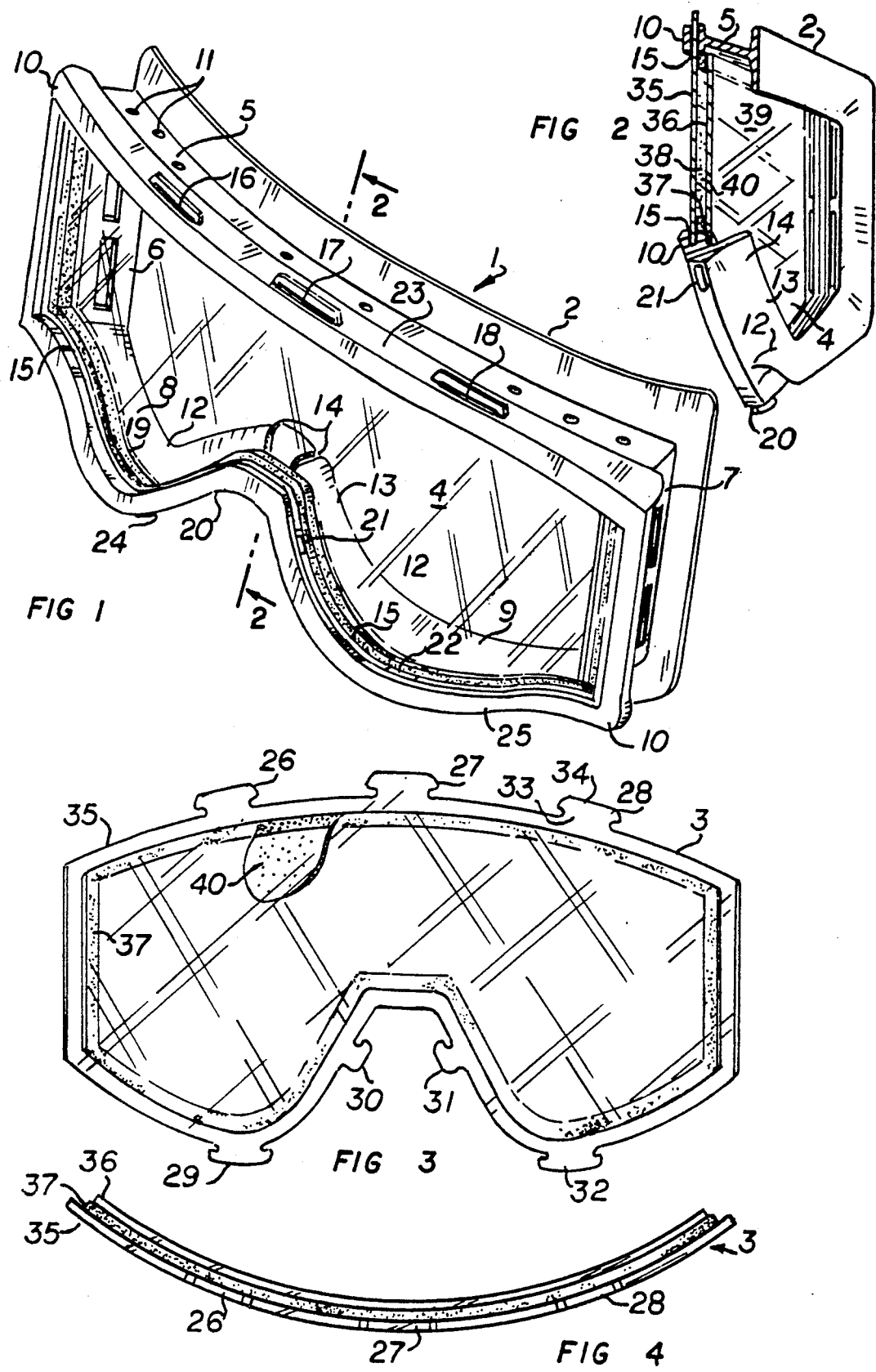
FIG. 1 is a perspective view of a preferred embodiment in accordance with the present invention.
FIG. 2 is a cross-sectional view thereof, taken along the line 2—2 of FIG. 1.
FIG. 3 is a back elevational view of the lens.
FIG. 4 is a top plan view thereof.

Referring now to the drawing, there is shown in FIG. 1 a pair of sport goggles, the frame 2 of which is made of elastomeric material of high flexibility and resiliency. The frame is adapted to receive the composite cylindrical lens 3 illustrated in FIGS. 3 and 4. The geometry of the frame 2 and of the lens 3 are further illustrated in the cross-sectional view of FIG. 2.

The frame 2 is shaped to follow the wearer's face from the lower forehead area above the eyebrows, around the eye depressions, along the cheek bones and around the base of the nose. This frame has a wide open aperture 4 which has the general shape of a lying-B designed to expose the eye depressions from the eyebrows to the base of the nose. Walls 5, 6, 7, 8 and 9 project forwardly from the face of the wearer, and generally orthogonally from it, above, on either side and at the base of the aperture respectively. The walls terminate in a rim 10 which forms a bead capping the walls and framing the lens 3. Various small apertures 11 are provided within the walls for ventilation purpose. The bottom walls 8 and 9 merge at 12 to form an inverted V-saddle which rests on the bridge of the nose. Slot 14 near the apex of the saddle 13 provides additional flexibility to intimately conform to the wearer's facial features. A groove 15 running along the inner face of the rim 10 is shaped and dimensioned to capture the peripheral edges of the lens 3. A plurality of slots 16–22 are cut at spaced-apart locations through the rim 10 from the bottom of the groove to the outer surface 23 24 and 25 of the rim 10. The slots are positioned, shaped and dimensioned to tightly engage tabs 26–32 which extend from the periphery of the lens 3. Each tab has a neck 33 which is commensurate with the width and depth of the corresponding slot and an enlarged head 34 which securely prevents dislodging the lens, except by flexing and stretching a section of the rim 10 around each slot.

The composite lens 3 comprises inner and outer transparent lenses 35 and 36 which are sealed together at their outer periphery by a spacing seal 37. The peripheral edges of the outer lens 35 includes a margin which extends beyond the seal and the edges of the inner lens 36 to engage the groove 15 of the frame 2, with the tabs 26–32 passing through the slots 16–22. In this configuration, the composite lens 3 can be mounted in a frame basically designed to mount a single lens. A spacer 37 and inner lens 36 have an outside dimension and contour which is commensurate with the space defined by the walls 5–9 of the frame 2. The thickness of the seal 37 forms an interstice which defines an insulating air-space between the lenses 35 and 36. The seal 37 is preferably made of close cell foam or any other resilient material bonded on either side to the lenses 35 and 36. The lenses 35 and 36 are preferably made from polycarbonate synthetic material having a thickness of 1.5 to 2 mm.

Due to perspiration, the area 39 between the face of the wearer and the composite lens becomes moisture-laden. A difference between the ambient temperature and the enclosed area 38 could cause the lens to fog and more particularly the inner lens 36. To prevent fogging of the inner lens 36 the goggles of the present invention further include a semi-transparent metal film 40 deposited against the inner surface of the outer lens 35. This metal film 40 has the property to reflect the body heat radiated by the wearer and thereby, to increase the temperature of the intertiscial space 38 between the two lenses. The temperature differential between the ambient air and more particularly between the inner lens 36 and the area 39 enclosed by the goggles is thus sufficiently reduced to prevent fogging of the inner lens 36. In the goggles of the present invention, the two lenses are sealed with very dry air to prevent fogging on the inside of either lens. Furthermore, the preferred embodiment is so designed as not to allow any leak or air inside the interstice 36 which would cause fogging inside the composite lens.

The heat-reflecting metal coating 40 is preferably a defused gold film which provides good reflective properties without substantial loss of transparency. The film 40 is vacuumdeposited on the lens according to conventional coating techniques.

The present invention, with or without the inner lens 36, is also effective in preventing fogging of any corrective eyeglasses that may be worn under the goggles 1. Any infrared radiation emitted by the face of the wearer and reflected by the film 40 will not only raise the temperature of the inner lens 36, if such lens is present, but would also impinge upon the outer face of the corrective eyeglasses.

While the preferred embodiment of the invention has been described it should be noted that the term "goggles" includes any type of face mask for sports or industrial applications. Although goggles lenses are typically non-refracting, the term lens hereinbefore used in this disclosure, includes refracting as well as non-refracting lenses. It is also to be understood that various modifications may be made and other embodiments may be devised without departing from the spirit of the invention and the scope of the appended claims.

What is claimed is:

1. Goggles adapted for use in cold weather which comprise:
   a lens assembly;
   an elastomeric pliable frame having ventilating apertures therethrough, said frame peripherally mounting said lens assembly, wherein said lens assembly comprises:
   a first lens having an outer face exposed to ambient air and an opposite inner face;
   a heat-reflective, semi-transparent coating applied to said inner face;
   a heat-conductive second lens inwardly parallel and spaced-apart from said first lens, said second lens being devoid of any reflective coating;
   a peripheral spacing seal hermetically closing an interstice between said first and second lenses, and
   wherein said first lens has a peripheral margin extending beyond the edges of the second lens; and
   said frame having a peripheral groove shaped and dimensioned to engage said margin.

2. The goggles of claim 1, wherein said reflective coating is made of defused gold particles.

3. An anti-fogging lens assembly for goggles used in cold weather which consists of:
   a heat-reflective first lens having an outer face exposable to ambient air, and an opposite inner face having a reflective coating applied thereto;
   a heat-conductive second lens inwardly parallel and spaced-apart from said first lens, said second lens being devoid of any reflective coating; and
   a peripheral spacing seal hermetically closing an interstice between said first and second lenses.

* * * * *